United States Patent [19]
Ishino et al.

[11] Patent Number: 5,753,482
[45] Date of Patent: May 19, 1998

[54] METHOD FOR CLONING OF A GENE FOR POL I TYPE DNA POLYMERASE

[75] Inventors: Yoshizumi Ishino, Takatsuki; Takashi Uemori, Otsu; Kayo Fujita, Shiga-ken; Ikunoshin Kato, Uji, all of Japan

[73] Assignee: Takara Shuzo Co., Ltd., Japan

[21] Appl. No.: 428,823

[22] Filed: Apr. 25, 1995

Related U.S. Application Data

[62] Division of Ser. No. 208,036, Mar. 9, 1994, Pat. No. 5,436,326, which is a continuation of Ser. No. 887,282, May 22, 1992, abandoned.

[30] Foreign Application Priority Data

| Jun. 3, 1991 | [JP] | Japan | 3-157368 |
| Nov. 7, 1991 | [JP] | Japan | 3-318685 |
| Feb. 24, 1992 | [JP] | Japan | 4-72090 |
| Feb. 25, 1992 | [JP] | Japan | 4-73161 |
| Apr. 6, 1992 | [JP] | Japan | 4-112400 |

[51] Int. Cl.$^6$ .................... C12N 9/12; C12N 15/54
[52] U.S. Cl. ....................... 435/194; 536/23.2
[58] Field of Search ............... 435/194; 536/23.2

[56] References Cited

U.S. PATENT DOCUMENTS

| 4,889,818 | 12/1989 | Gelfand et al. | |
| 5,210,036 | 5/1993 | Comb et al. | 435/194 |
| 5,242,818 | 9/1993 | Oshima et al. | 435/194 |

FOREIGN PATENT DOCUMENTS

| WO8906691 | 7/1989 | WIPO |
| WO9109950 | 7/1991 | WIPO |
| WO9203556 | 3/1992 | WIPO |

OTHER PUBLICATIONS

F.C. Lawyer et al., *J. Biol. Chem.*, 264(11), 6427–6437 (1989).
P. Lopez et al., *J. Biol. Chem.*, 264(7), 4255–4263 (1989).
C.M. Joyce et al., *J. Biol. Chem.*, 257(4), 1958–1964 (1982).
J.J. Dunn et al. *J. Mol. Biol.*, 166, 477–535 (1983).
J. Ito et al., *Nuc. Acids Res.*, 19(15), 4045–4057 (1991).
Y. Ishino et al., *FASEB Journal*, 6(1), A216 (1992).
A. Weerkamp et al., *J. Bacteriology*, 109(1), 443–446 (1972).
S.J. Gould et al., *Proc. Natl. Acad. Sci.*, 86:1934–1938 (1989).
J.H. Nunberg et al., *J. Virology*, 68(9), 3240–3249 (1989).
J.A. Sakanari et al., *Proc. Natl. Acad. Sci.*, 86:4863–4867 (1989).
Tang et al., Abstracts of the Annual Meeting of the American Society of Microbiology, 90 Meet., p. 214 (1990).
Zuli, et al., *Hoppe–Seyler Biol. Chem.*, 379(9), 1167–1177 (1987).
Haberstich et al., *Arch. Microbiol.*, 98(4), 275–287 (1974).
Wang et al., *FASEB Journal*, 3(1), 14–21 (1989).
Klimczak et al., "Purification and Characterization of DNA Polymerase From the *Archeaebacterium Methanobacterium thermoautotrophicum*", Biochemistry 25: 4850–4855, Aug. 1986.
Simpson et al., "Purification of a Thermostable DNA Polymerase From a Thermotoga Species", Ann. NY Acad. Aci. 613: 426–428, 1990.
Hamal et al., Purification and Characterization of DNA Polymerase From the Archaebacterium *Thermoplasm acidophilum*, Eur.J. Biochem. 190: 517–521, Jul. 1990.
Ruttimann et al., "DNA Polymerase From the Extremely Thermophilic Bacterium *Thermus thermophilus* HB-8", Eur. J. Biochem. 149: 41–46, May 1985.
J.D. Wisotzkey et al., "16S rRNA Phylogenetic Relationships Among the Thermophilic Bacillus Species", Absts. Gen. Met. Am. Soc. Microbiol. 91: 244, Abst. #R–17, May 1991.
J. McClary et al., "Sequencing with the Large Fragment of DNA polymerase I from *Bacillus stearothermophilus*", DNA Sequence 1(3) 173–180, 1991.
J. Stenesh et al., "DNA Polymerase from Mesophilic and Thermophilic Bacteria. I. Purification and Properties of DNA Polymerase from *Bacillus licheniformis* and *Bacillus stearothermophilus*", Biochim. Biophys. Acta 272 156–166, Jun. 1972.

*Primary Examiner*—Rebecca E. Prouty
*Attorney, Agent, or Firm*—Wenderoth, Lind & Ponack

[57] ABSTRACT

The present invention is directed to a method for cloning a gene for Pol I type DNA polymerase comprising;
(a) amplifying target DNA with PCR using primers specific to said genes;
(b) cloning a gene for Pol I type DNA polymerase with a probe selected from amplified DNA. And this invention is directed to a novel isolated gene coding for Pol I type DNA polymerase cloned in the plasmid.

1 Claim, 2 Drawing Sheets

METHOD FOR CLONING OF A GENE FOR POL I TYPE DNA POLYMERASE

This is a divisional application of Ser. No. 08/208,036, filed Mar. 9, 1994 now U.S. Pat. No. 5,436,326; which is a continuation of now abandoned application Ser. No. 07/887,282, filed May 22, 1992.

FIELD OF INDUSTRIAL USE

This invention relates to a method how to clone the genes for Pol I type DNA polymerases, which are very useful for genetic engineering research, and also relates to genes that code for new Pol I type DNA polymerase.

STATE OF THE PRIOR ART

On the basis of segmental similarities in the amino acid sequences, DNA polymerases have been classified into two major groups; the Escherichia coli DNA polymerase I family (Pol I type) and the eukaryotic DNA polymerase α family (α type).

DNA polymerases, which are widely used as a reagent in genetic engineering research, currently include DNA polymerase I from Escherichia coli; Klenow fragment, which is a modified form; DNA polymerase from T4 phages; DNA polymerase from T7 phages; heat-stable DNA polymerase from Thermus aquaticus (Taq polymerase); etc. Most of those belong to the Pol I family. These enzymes are used to label specific DNA or in the identification of DNA base sequences, according to their enzymatic properties.

PROBLEM TO BE SOLVED BY THE INVENTION

In general, methods for the use of DNA polymerase differ depending on the specificity of the enzyme, which varies for enzymes of different origins. For example, Bacillus caldotenax has an optimum temperature for growth of about 70° C., so the Pol I type DNA polymerase from this bacterium is probably stable at high temperature, and it should be useful as a reagent for use in genetic engineering research.

However, details about the properties of this DNA polymerase are not known, and a method for its preparation is not available. The structure of the gene that codes for this DNA polymerase and the amino acid sequence of the enzyme are not known, and a method has not been established by which the gene can be isolated, ligated with a vector, and expressed by genetic engineering.

The purpose of this invention is to provide a simple and efficient method for cloning genes that code for novel Pol I type DNA polymerases and to provide the sequence of the gene that codes for a novel Pol I type DNA polymerase.

STEPS TAKEN TO SOLVE THE PROBLEM

To summarize this invention, first, this invention relates to a method for cloning of a gene coding for Pol I type DNA polymerase which comprises the following steps of:
(a) amplifying target DNA with Polymerase Chain Reaction using a primer represented SEQ ID No. 1 or SEQ ID No. 2;
(b) cloning a gene of Pol I type DNA polymerase by conventional method with a probe selected from an amplified DNA of step (a).

Secondly, this invention relates to isolated gene coding for a Pol I type DNA polymerase, wherein the isolated gene is obtainable from the plasmid pUI101 or pUI205.

Third, this invention relates to isolated gene for coding a Pol I type DNA polymerase characterized by the fact that said gene can hybridize with the gene of the second invention in a stringent condition.

The inventors of this invention achieved the invention, a method for the cloning of the gene for Pol I type DNA polymerase with ease and effectively even if the structure of the gene and the amino acid sequences of the gene product of the desired Pol I type DNA polymerase gene are unknown, by designing a pair of primers for use in the amplification of the DNA polymerase genes by the PCR, and with the use of said pair of primers, it is possible to amplify a portion of unknown DNA polymerase genes, and the desired gene for Pol I type DNA polymerase can be cloned with the use of the amplified gene as a probe; by cloning of the gene, it is possible to obtain Pol I type DNA polymerase by the methods of genetic engineering at high yield.

Below, this invention is described in detail.

As the method for the selection of the desired DNA fragments, first, the published amino acid sequences of known Pol I type DNA polymerases are compared with each other, and on the basis of common amino acid sequences that are found, oligodeoxyribonucleotides are synthesized. The amino acid sequences of Pol I type DNA polymerases can be found in, for example, Journal of Biological Chemistry, vol. 257, 1958–1964 (1982), Journal of Molecular Biology, vol. 166, 477–535 (1983), Journal of Biological Chemistry, vol. 264, 6427–6437 (1989), and Journal of Biological Chemistry, vol. 264, 4255–4263 (1989). They are the sequences of DNA polymerases from Escherichia coli, T7 phage, Thermus aquaticus, and Streptococcus pneumoniae, respectively.

The sequences shown as SEQ ID Nos. 1 and 2 in the sequence listing are the sequences of mixed primers for use in the PCR that were designed on the basis of conserved sequences in Pol I type DNA polymerases by the inventors of this invention. The sequence shown as SEQ ID No. 1 in the sequence listing is a mixed primer found by the inventors to be a conserved sequence in Pol I type DNA polymerases; that is, it was designed on the basis of amino acid sequences shown as SEQ ID Nos. 3–6 in the sequence listing. The sequence shown as SEQ ID No. 2 in the sequence listing is a mixed primer found to be a conserved sequence at another region of Pol I type DNA polymerases; that is, it was designed on the basis of amino acid sequences shown as SEQ ID Nos. 7–10 in the sequence listing. This pair of primers can be used to amplify the Pol I type DNA polymerase gene from, for example, Escherichia coli, T7 phage, Thermus aquaticus, and Streptococcus pneumoniae with efficiency. It is possible to use said pair of primers as primers in the PCR done to clone the Pol I type DNA polymerase gene. The primers that can be used in this invention can be any primers that can hybridize with the conserved sequences of said genes and amplify said genes with efficiency, any primers derived from the mixed primers described above, any primers designed on the basis of other conserved sequences, or any combination of primers designed from conserved sequences and vectors.

Cloning of the genes for Pol I type DNA polymerases, transformation of the E. coli host strain by the plasmid containing the genes for the polymerases, and the purification of the polymerases can be performed by the following steps, given as an example.

1. Chromosomal DNA is isolated from cells having any Pol I type DNA polymerase.
2. Oligonucleotide primers for use in Pol I type DNA polymerase gene amplification shown as SEQ ID Nos. 1 and 2 in the sequence listing, which sequences are based on the region coding for DNA polymerase, are prepared.

and the polymerase chain reaction is performed with the DNA obtained in step 1 above as the template.

3. The DNA obtained in step 1 above is cleaved with suitable restriction enzymes, the fragments obtained are used as probes to screen the DNA fragments obtained in step 2, and the desired DNA fragments are obtained.
4. Vectors are cleaved by an appropriate restriction enzymes, and the DNA obtained in step 3 is ligated into the cleaved site.
5. Vectors with the ligated DNA fragments are introduced into host cells, and transformants that contained the desired DNA fragments are selected.
6. Plasmids are isolated from the transformants produced in step 5, the desired DNA fragments are removed, if necessity, and on the basis of the restriction map, the desired gene is recreated in its entirety as a continuous genomic fragment, and this is ligated as summarized in step 4 in an expression vector.
7. Expression vectors carrying the desired DNA fragment are introduced into host cells as described in step 5 to give transformants.
8. The transformants obtained in step 7 are cultured, and produce DNA polymerase in *E. coli* cell.
9. Exonuclease III is used, if necessity, to produce polymerase in which the 5'43 3'-exonuclease coding region is missing from the region coding for entire DNA polymerase.
10. The expression vectors obtained in step 9 are introduced into host cells to produce transformants, and the transformants produce mutant DNA polymerase.
11. The transformant obtain ed in step 10 is cultured and the mutant DNA polymerase is purified from the cultured cells.

The bacterial strain that is used in this invention can be any bacterial strain that produces DNA polymerase, such as, for example, *Bacillus caldotenax* YT-G (Deutsche Sammlung von Mikroorganismen accession number DSM406).

Below is the explanation of this invention using *B. caldotenax* YT-G as one example.

DNA from the strain used to produce the desired DNA, *B. caldotenax* YT-G (DSM406), is extracted from a bacterial culture that has been cultivated with shaking at 70° C. Extraction, purification, the cleaving with restriction enzymes, and the like can be done by any of the published methods, such as those published in *Molecular cloning: A laboratory manual* by T. Maniastis et al., on pages 75-178 (Cold Spring Harbor Press, 1982).

The inventors of this invention used as primers the two oligonucleotides with the SEQ ID Nos. 1 and 2 in the sequence listing, which are based on the common amino acid sequences found by comparison. The inventors used DNA from *B. caldotenax* as the template in the PCR to amplify specific DNA fragments, and found that the amino acid sequence deduced from the base sequence of the DNA fragments obtained was very similar to that of other known DNA polymerases. Said DNA fragments can be used as probes in hybridization to select the desired DNA. The hybridization method used for selection can be any of the published methods, such as that on page 309 of the book mentioned above, *Molecular cloning; A laboratory manual.*

By Southern hybridiztion, the gene for the desired DNA polymerase can be located in restriction fragments from *B. caldotenax*, and the selected restriction enzymes, such as EcoRI, BamHI, HincII, HindIII, XhoI, PstI, and PvuII, can be used to digest *B. caldotenax* DNA, which is then ligated to plasmid vectors. The plasmid vectors can be any of the known ones, such as, for example, pUC18, pUC19, pTV118N, etc.; the plasmid vectors that can be used are not limited to this list. The procedure used to insert the DNA fragment can be any of the known methods, such as by use of an enzyme reaction with DNA ligase for the insertion.

Next, the recombinant plasmids are introduced into host cells of *Escherichia coli*, or into any wild strain or mutant strain of host cells that can be transformed; it is preferable to use a mutant defective in the restriction system (restrictions⁻, modification⁺). The procedure used for the introduction can be any of the known methods, such as that on page 250 of the book mentioned above, *Molecular cloning; A laboratory manual.*

In this way, the desired DNA fragment is introduced into host cells, and clones are selected according to the characteristics of the plasmid vector used; for example, when pUC18 is used, colonies are selected for ampicillin resistance. By this method, it is possible to obtain groups of cells in which the desired DNA is cloned. From the colonies obtained, clones that have the desired fragment can be selected. The method of selection is by colony hybridization with a variety of vectors, and if plaque hybridization is used, any of the published methods can be used.

Three clones were selected, and digestion with restriction enzymes and analysis of the findings obtained (that they had HincII fragments, HindIII fragments, or XhoI fragments) gave the basis on which the three fragments were relinked in the test tube, giving one continuous DNA fragment, which DNA fragment was ligated with the expression vector pTV118N, giving a desired clone. This plasmid produced in this way was designated pUI101.

Cells of *E. coli* containing plasmid pUI101 were cultured, and a crude extract of the harvested cells was obtained.

The extract was treated at 60° C. for 20 minutes, after which heat treatment DNA polymerase activity was still found, although a cell extract from *E. coli* with the expression vector alone (without the desired DNA fragment) had no such activity. This showed that the bacterial cells carrying pUI101 produced a heat-resistant DNA polymerase, and that the gene for the coding of this enzyme was in fact expressed in the cells of *E. coli*.

The construction of plasmid pUI101 was as shown in FIG. 1. The gene that coded for DNA polymerase was in an NcoI fragment of about 3.5 kilobases in plasmid pUI101, and the restriction map of said NcoI fragment is shown in FIG. 2. Its base sequence is shown as SEQ ID No. 11 in the sequence listing. The cells of *E. coli* that grew best as host cells when transformed with pUI101 were *E. coli* HB101, and the transformed cells were designated *Escherichia coli* HB101/pUI101, and deposited as FERM BP-3721 at the Fermentation Research Institute, Agency of Industrial Science and Technology, Japan.

When *E. coli* cells carrying pUI101 are cultured, it is possible to obtain heat-resistant DNA polymerase from the cultured cells, which express a large amount of such heat-resistant DNA polymerase. The method for the purification of the DNA polymerase can be, for example, sonication of the cultured cells, heat-treatment of the sonicated suspension, column chromatography on DEAE-cellulose, column chromatography on phosphocellulose to give a single band of DNA polymerase on SDS-polyacrylamide gel electrophoresis (SDS-PAGE).

The DNA polymerase obtained is a polypeptide that is in the position of the molecular weight of 100,000 by SDS-PAGE. Its DNA synthetic activity includes that of 3'–5'-exonuclease and that of 5'→3'-exonuclease.

The amino acid sequence of the purified protein obtained was analyzed, and it was possible to identify the N-terminal amino acid sequence. The sequence is shown as SEQ ID No. 12 of the sequence listing. This amino acid sequence was found in the translational frame of the NcoI fragment mentioned above, the sequence of which is SEQ ID No. 13 of the sequence listing. The structural gene of the DNA polymerase of this invention was identified, and its entire amino acid sequence was found and is shown as SEQ ID No. 14 in the sequence listing.

When DNA polymerase from *E. coli* transformants was studied, it seemed that the 5'→3'-exonuclease activity was present in a domain at the amino-terminal of the polypeptide, so DNA fragments from *B. caldotenax* in pUI101 were prepared that had a defined portion of the DNA fragment missing, and these were used to transform *E. coli*, which still had DNA synthetic activity, but clones that lacked 5'→3'-exonuclease activity could be selected. To prepare the deletion plasmid, the method of Henicoff published in *Gene*, vol. 28, 351–359 (1982) can be used. The plasmid selected was designated pUI205, and used to transform *E. coli* cells, which were deposited as *Escherichia coli* HB101/pUI205 (FERM BP-3720) at the Fermentation Research Institute, Agency of Industrial Science and Technology, Japan.

*E. coli* cells carrying pUI205 can be cultured, and heat-resistant DNA polymerase can be obtained from the cultured cells, which express a large amount of such heat-resistant DNA polymerase. It is possible to purify the DNA polymerase from the cultured cells by the methods described above or the like until the enzyme gives a single band on SDS-PAGE.

By amino acid analysis of the purified protein, it is possible to identify the N-terminal amino acid sequence. This sequence is shown as SEQ ID No. 15 in the sequence listing. This sequence is lacking the 284 amino acids from Met 1 to Lys 284 of SEQ ID No. 14 of the sequence listing. The entire amino acid sequence of the gene that codes for this mutant form of DNA polymerase has been identified. SEQ ID No. 16 of the sequence listing is the base sequence coding for the mutant DNA polymerase, and SEQ ID No. 17 of the sequence listing is the amino acid sequence of the mutant form of the enzyme.

It is possible to prepare the heat-resistant enzymes on an industrial scale, because by the cultivation of *E. coli* HB101/pUI101 or *E. coli* HB101/pUI205, 1 ml of culture broth gave 127 units or 212 units of DNA polymerase activity (the non-mutant form and the mutant form, respectively).

As described above in detail, with this invention, the following usual steps for cloning of the gene for Pol I type DNA polymerase are not needed:

(a) checking for the production of Pol I type DNA polymerase;
(b) isolation of the enzyme;
(c) identification of a partial amino acid sequence;
(d) synthesis of a probe from the identified amino acid sequence.

Without use of these steps, the gene for the desired Pol I type DNA polymerase can be simply and effectively obtained.

Examples

Figure 1:
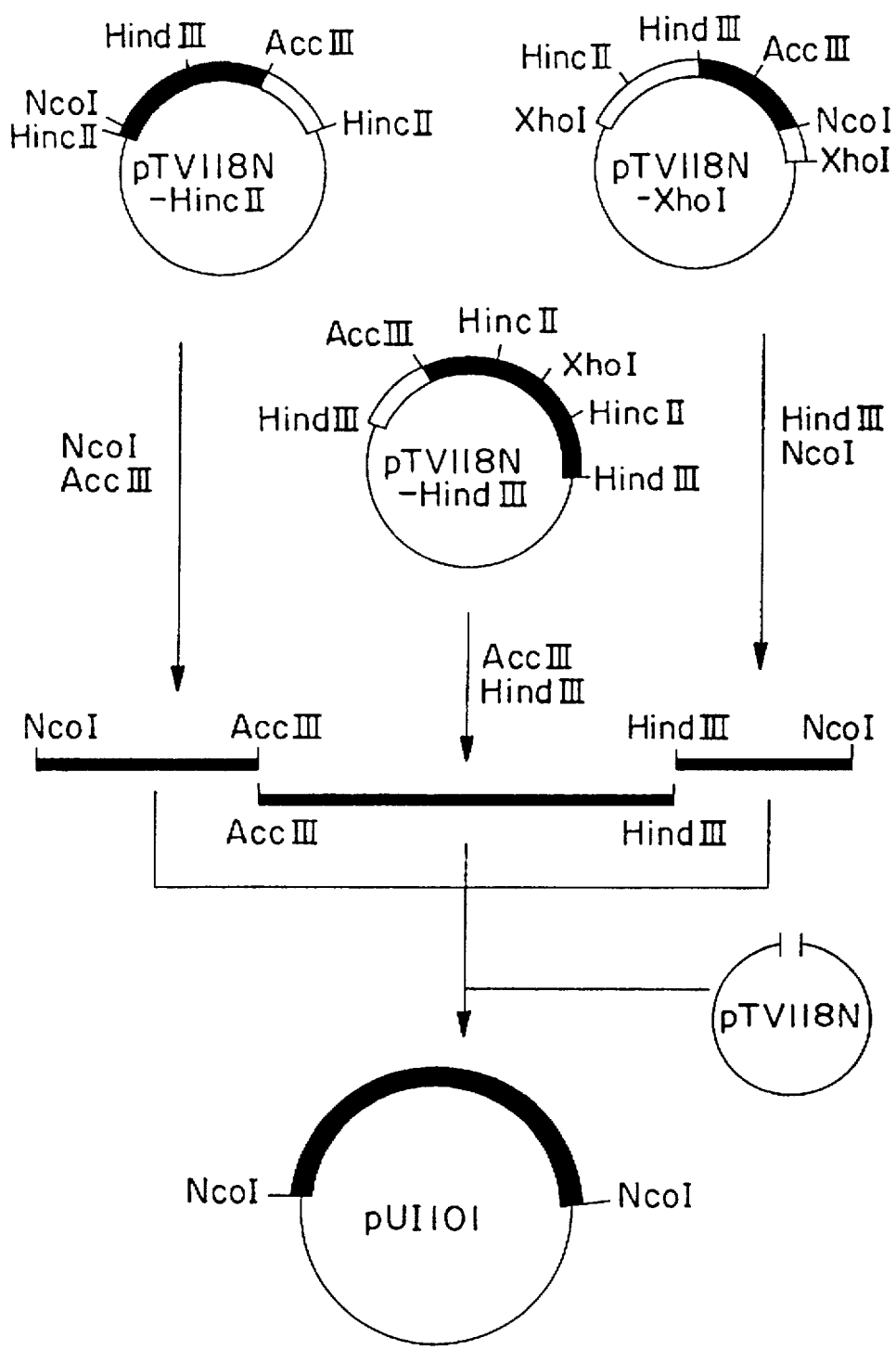
FIG. 1 is a diagram of the procedure used to construct pUI101.

Below, this invention will be explained with reference to examples, but the invention is not to be taken to be limited to these examples.

Example 1

Two oligodeoxyribonucleotides having the sequences that are shown as SEQ ID No. 1 and No. 2 in the sequence listing were synthesized and purified for PCR primers. In the next step, PCR were done using genomic DNAs prepared from *E. coli*, T7 phage, *T. aquaticus*, *T. thermophilus*, *S. pneumoniae*, *Bacillus subtilis*, *B. stearothermophilus*, *B. caldolyticus*, *Lactobacillus bulgaricus*, *L. homohiochii*, and *L. heterohiochii*, as templates. Each reaction mixture included 100 pmol of each oligonucleotide primer and 1 ng of the genomic DNA in 100 volumes. Thirty cycles of the carried out, with each cycle consisting of 30 sec at 95° C., 1 min at 55° C., and 2 min at 72° C. Then 5 μl portions of each reaction mixture were put directly on a 0.8% agarose gel. All of these PCR reactions resulted in about 600 bp product. These fragments were cloned into SmaI site of M13 vector and determined the nucleotide sequences.

Example 2

2-1. Preparation of chromosomal DNA from *B. caldotenax*

First, *B. caldotenax* YT-G was grown in 125 ml of L medium (10 g/l Bactotryptone, 5 g/l yeast extract, and 5 g/l NaCl, at pH 7.2) at 65° C. overnight with shaking, and the bacterial cells were harvested and suspended in 4 ml of 25% sucrose containing 0.05M Tris-HCl (pH 8.0). To the suspension, 800 μl of lysozyme (5 mg/ml) was added, and the mixture was left at 20° C. for 1 hour. Then 24 ml of SET solution (20 mM Tris-HCl, pH 8.0, 1 mM EDTA, and 150 mM NaCl) was added, after which 4 ml of 5% SDS and 400 μl of proteinase K (10 mg/ml) were added, and the mixture was kept at 37° C. for 1 hour. After phenol extraction and chloroform extraction, ethanol was added to precipitate long fragments of DNA, which were removed from the suspension with a sterilized toothpick. By this procedure, 3.1 mg of DNA was obtained.

2-2. Amplification of specific DNA by the PCR

With 100 pmol of each of the two oligodeoxyribonucleotides shown in the sequence listing as SEQ ID Nos. 1 and 2, and with 1 ng of DNA from *B. caldotenax* in a total volume of 100 μl, 30 cycles of the PCR were carried out, with each cycle consisting of 30 seconds at 95° C., 1 minute at 55° C., and 2 minutes at 72° C. Then 5 μl of the reaction mixture was sampled and analyzed by agarose gel electrophoresis. The analysis showed that a DNA fragment 600 base pairs long had been amplified specifically. This DNA fragment was ligated into M13mp18, the phage vector having been cleaved with SmaI. The base sequence was found by the dideoxy method.

2-3. Detection of the desired gene by the genomic Southern method.

DNA from *B. caldotenax* was digested with 5 μg of each of the following enzymes: EcoRI, BamHI, HindIII, HincII, XhoI, PstI, and PvuII. The digest was treated by agarose gel electrophoresis. The DNA in the gel was transferred to a nylon membrane, and then hybridization was done with the DNA fragment of 600 base pairs described above as being obtained by the PCR as the probe. The probe was labelled radioactively by the random priming method. Hybridization was done in 6× SSC that contained 1% SDS, 5× Denhardt's, solution, and 10 μg/ml calf thymus DNA at 65° C. for 5 hours. Then the membrane was washed in 1× SSC containing 0.1% SDS for 1 hour, and used to expose X-ray film, giving an autoradiogram.

2-4. Cloning of DNA fragments containing the gene for DNA polymerase

To clone the DNA fragments found to be positive during genomic Southern analysis, the 2.40-kb HindIII fragment, the 1.45-kb HincII fragment, and the 2.1-kb XhoI fragment of DNA from *B. caldotenax* were obtained by digestion of 100 μg of each DNA with the necessary restriction enzyme (HindIII, HincII, or XhoI) as appropriate, and the DNAs of the desired sizes were obtained by electrophoresis on agarose gel. Collections were done by adsorption onto glass beads. Plasmid pTV118N was linearized with the same three enzymes, and alkaline phosphatase was used to remove the phosphorylated residues at the terminals. Then the DNA was ligated to the vector with DNA ligase, and the vectors were introduced into cells of *E. coli* JM109. The transformants obtained were then treated by colony hybridization for selection of the desired clones.

From 50 to 200 colonies of recombinants grown on a nylon membrane were denatured in a mixture of 0.5N sodium hydroxide and 1.5M sodium chloride, and were then neutralized with a mixture of 1M Tris-HCl and 1.5M sodium chloride (pH 7.0). DNA was fixed on the membrane with ultraviolet light. The preparation of the probe and the hybridization conditions were the same as those used in genomic Southern analysis.

2-5. Restriction analysis of cloned fragments and reconstitution of the DNA polymerase gene From the results of restriction mapping of the three DNA fragments obtained, it was found that the fragments overlapped when arranged in the order of the HincII fragment, the HindIII fragment, and the XhoI fragment. The fragments formed a continuous part of the chromosomal DNA. Restriction sites were selected so that unneeded portions would be eliminated as far as possible, and the three DNA fragments were ligated with the vector pTV118N at the same time, as shown in FIG. 1. In this way, a plasmid that contained about 3.5 kb of DNA fragment that included the gene for DNA polymerase was constructed and designated pUI101.

Figures 2, 3:
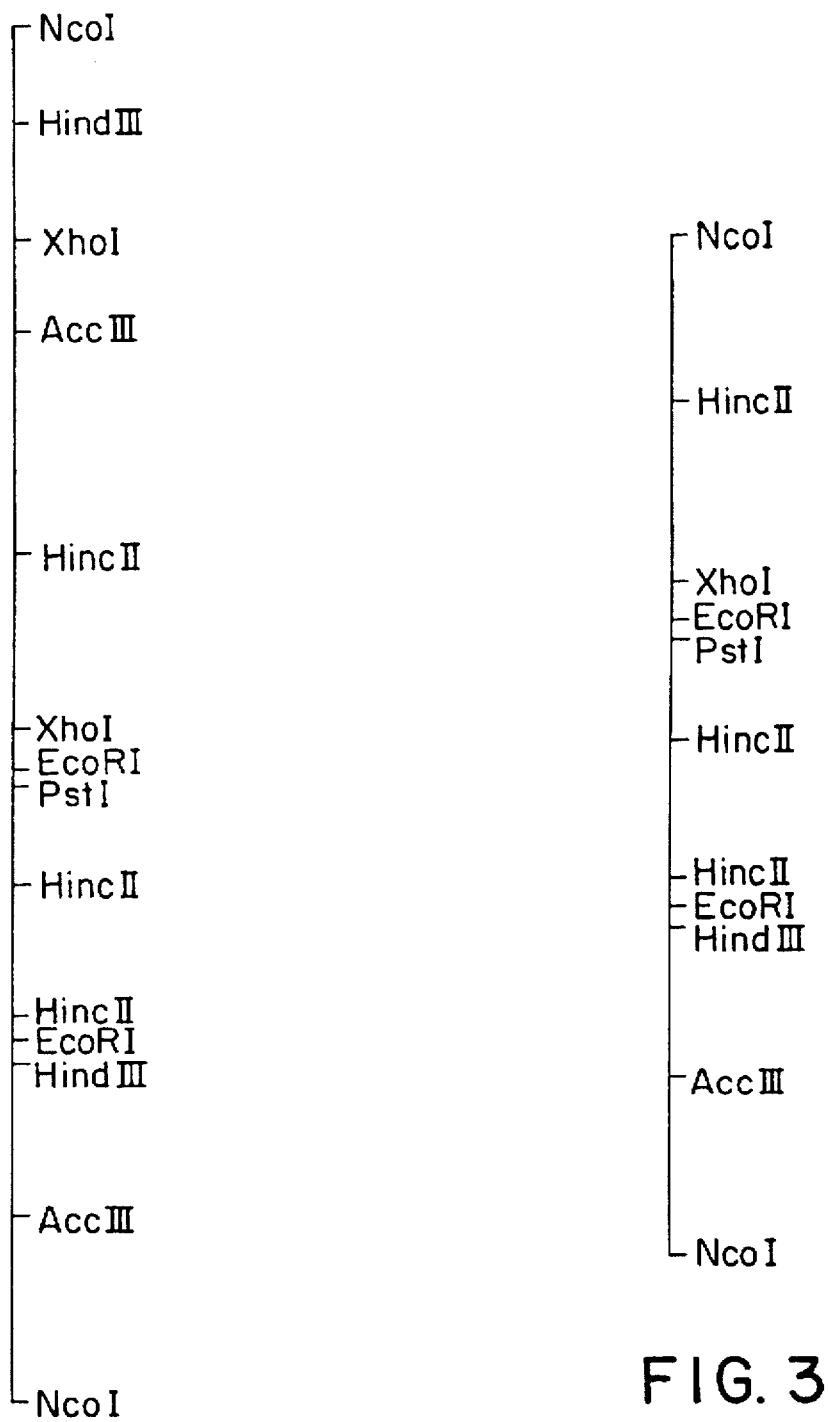
FIG. 2 is a restriction map of the gene for DNA polymerase cloned in pUI101.
FIG. 3 is a restriction map of the gene for DNA polymerase cloned in pUI205.

FIG. 1 shows the construction of pUI101. FIG. 2 shows the restriction map of the NcoI DNA fragment, which included the gene for DNA polymerase, that was cloned in pUI101.

Next, said plasmid was used to transform cells of *E. coli* HB101, and the transformants were deposited as *Escherichia coli* HB101/pUI101 (FERM BP-3721).

2-6. Culture of transformants and preparation of a crude extract Cells of *E. coli* HB101 (FERM BP-3721), which contained the recombinant plasmid pUI101 described above, were cultured at 37° C. in 5 ml of L medium that contained 100 μg/ml ampicillin. When the absorbance of the culture broth reached 0.6 ($A_{600}$), isopropyl-β-D-thiogalactoside (IPTG), the derivative of the substrates for β-galactosidase, was added to the culture, and culture was continued for 15 hours more.

Cells in 1 ml of culture broth were harvested and washed in 50 mM Tris-HCl (pH 8.0) containing 25% sucrose. The cells were lysed again in the same solution, to which the same volume of lysis solution (50 mM Tris-HCl, pH 7.5, 25% sucrose, 60 mM spermidine-HCl, 20 mM sodium chloride, and 12 mM dithiothreitol) was added, and the mixture was left for 45 minutes at 4° C. Then 20 μl of 5% (w/v) Triton X100 was added to the mixture, which was left for 5 minutes at 37° C. The supernatant obtained by centrifugation was incubated for 20 minutes at 60° C., and centrifuged again. The supernatant obtained in this step was the crude extract.

2-7. Assay of DNA polymerase activity

A reaction mixture was prepared that contained 67 mM potassium phosphate, pH 7.4, 6.7 mM magnesium chloride, 1 mM 2-mercaptoethanol, 20 μM activated DNA, 33 μM each dATP, dCTP, dGTP, and TTP, and 60 nM [$^3$H]TTP. An appropriate amount of the crude extract was added to 150 μl of this solution, and reaction was allowed to proceed for 5 minutes at 60° C., after which the reaction was stopped by the addition of 1 ml of a mixture of 50 mM pyrophosphoric acid and 10% trichloroacetic acid. The reaction vessel was placed in ice for 5 minutes, and the entire reaction mixture was filtered on a glass filter under reduced pressure. The filter was washed several times with 10% trichloroacetic acid, and then with 70% ethanol before being dried and put in a liquid scintillation counter for the counting of radioactivity. There were 127 units of DNA polymerase activity in 1 ml of culture broth.

2-8. Production of heat-resistant DNA polymerase by *E. coli* cells carrying plasmid pUI101.

From 2.2 g of cells of *E. coli* HB101/pUI101, 20 ml of crude extract was obtained by the methods described in Example 2-6. This extract was incubated at 60° C. for 30 minutes, and the protein denatured by heat was removed by centrifugation for 10 minutes at 10000×g. To the supernatant, ammonium sulfate was added, and the fraction that precipitated at 30–80% saturation was dialyzed against DE buffer (50 mM Tris-HCl, pH 7.0, 0.2 mM 2-mercaptoethanol, 10% glycerol, and 4 μM phenylmethanesulfonyl fluoride). Then the same buffer was used to equilibrate a column of 15 ml of DE52 (Whatman) and the extract was eluted from the column with a linear gradient of NaCl concentrations from 0 to 300 mM. Then the DNA polymerase activity was assayed by the method of Example 2-7. The fractions of DE buffer that contained activity were pooled and put on a column of 15 ml of P11 (Whatman) equilibrated with DE buffer. Then elution was done with a linear gradient of NaCl concentrations from 0 mM to 300 mM, and the fractions with activity were pooled. The P11 fractions were analyzed by SDS-PAGE, and a single band at the molecular weight of 100,000 was found.

2-9. Identification of the N-terminal amino acid sequence by an amino acid analyzer The DNA polymerase obtained in example 2-8 was analyzed with an amino acid analyzer, and the amino acid sequence of the N-terminal region was that shown as SEQ ID No. 12 in the sequence listing.

Example 3

3-1. Preparation of plasmids with a regional deletion To eliminate 5'→3'-exonuclease activity, which was deduced to be present at a domain in the amino-terminal side of DNA polymerase protein, plasmids were prepared with regional deletions from the 5'-end of the gene. So that the method that uses exonuclease III could be employed, first, the NcoI fragment about 3.5 kb long carried by pUI101 was cut out and made blunt-ended, after which it was ligated at the HincII side of pTV118N. Then double digestion of the 3'-protruding ends with KpnI and of the 5'-protruding ends with XbaI was done, and exonuclease III was used to digest only the 3'-protruding ends. Mung bean nuclease was used to make blunt ends, and then DNA ligase was used to restore the original circular shape. By adjustment of the time of the exonuclease reaction, mutants with deletions of a variety of sizes could be obtained. By ligation with NcoI linker before recircularization, the initiation codon could be inserted in an appropriate location, and depending on the location of the deletion, the reading frame came to be that of the DNA polymerase gene in one-third of the cases (that is, the probability that the reading frames matched was one-third).

The plasmid constructed as described above was introduced into *E. coli* cells; of the transformants obtained, 20 clones were selected at random and their crude extract was prepared and assayed for DNA polymerase activity. There were DNA synthetic activities at 60° C., so the base sequences were analyzed. One of the clones with activity was selected and the carried plasmid was designated pUI205. The 2-kb DNA fragment shown in FIG. 3 was inserted into pUI205. Next, the plasmid was used to transform *E. coli* HB101 cells, and these were designated *Escherichia coli* HB101/pUI205 cells (FERM BP-3720).

FIG. 3 is a restriction map of the gene for DNA polymerase that was cloned into pUI205.

3-2. Culture of recombinants and preparation of crude extract

The recombinants mentioned above, FERM BP-3720, were cultured and a crude extract was prepared from the cultured cells by the methods of Example 2-6.

3-3. Assay of DNA polymerase activity.

The crude extract obtained above was assayed for DNA polymerase activity by the methods of Example 2-7. The crude extract had 212 units of DNA polymerase activity in 1 ml of culture broth.

3-4. Assay of 5'→3'-exonuclease activity

As a substrate, plasmid pBR322 was cleaved with PvuII, and the fragment 322 base pairs long was treated with [γ-$^{32}$P]ATP and polynucleotide kinase to phosphorylate it. Then the enzyme standard prepared in Example 3-2 were mixed with a solution containing 67 mM potassium phosphate (pH 7.4), 6.7 mM magnesium chloride, and 1 mM 2-mercaptoethanol and with the substrate, and reaction was allowed to occur for 5 minutes at 60° C. Then the substrate DNA was made to precipitate by the addition of ethanol.

The radioactivity in the supernatant was counted on a liquid scintillation counter, and the amount of product produced by exonuclease was calculated. In the enzyme used, 5'→3'-exonuclease activity was not detected.

3-5. Production of heat-resistant DNA polymerase by *E. coli* cells carrying plasmid pUI205

By the methods of Example 2-8, standard enzyme was obtained from cells of *E. coli* HB101/pUI205. The obtained enzyme was analyzed by SDS-PAGE, and it gave a single band at the molecular weight of 67,000.

3-6. Sequencing of the N-terminal sequence by an amino acid analyzer

By the methods of Example 2-9, the N-terminal amino acid sequence of the standard enzyme was found to be that shown as SEQ ID No. 15 in the sequence listing.

Example 4

4-1. Determination of the base sequence of the chromosomal DNA from *B. caldotenax* including the structural gene for DNA polymerase By the methods of Example 3-1, a number of deletion mutants of a variety of sizes were prepared, and their base sequences were identified by the dideoxy method. The data obtained were analyzed and the base sequence of the entire NcoI-NcoI fragment obtained from pUI101 was found to be that of SEQ ID No. 11 in the sequence listing. The sequence of pUI205 was found to be that of base numbers 1032–3252 of the NcoI fragment of pUI101 shown as SEQ ID No. 11 in the sequence listing.

Thus, based on the N-terminal amino acid sequence identified as described in Example 2-9, and Example 3-6, and the base sequence identified in this example, we identified the structural gene of the DNA polymerase of this invention and the amino acid sequence of the DNA polymerase of this invention.

As explained above in detail, this invention provides a simple and efficient method for cloning genes that code for novel Pol I type DNA polymerases and provides said genes. This invention also provides a method for production of a Pol I type DNA polymerase, which is useful as a reagent in genetic engineering research.

---

What we claim is:

1. An isolated and purified DNA polymerase having 3'→5' exonuclease activity and which has an amino acid sequence represented by SEQ ID NO:14 or SEQ ID NO:17 in the sequence listing.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( i i i ) HYPOTHETICAL:

( i v ) ANTI-SENSE: No ( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:1:

GA Y CCHAAC Y    TSCARAA Y AT  HCC                 23

( 2 ) INFORMATION FOR SEQ ID NO:2:

(i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: other nucleic acid (iii) HYPOTHETICAL:

(iv) ANTI-SENSE: Yes (v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:

-continued ( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:2:

K A S N A K Y T C R  T C R T G N A C Y T  G        2 1

( 2 ) INFORMATION FOR SEQ ID NO:3:

( i ) SEQUENCE CHARACTERISTICS:
        ( A ) LENGTH: 8 amino acid residues
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
        ( A ) ORGANISM: Escherichia coli
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:3:

Asp  Pro  Asn  Leu  Gln  Asn  Ile  Pro
 1                     5

( 2 ) INFORMATION FOR SEQ ID NO:4:

( i ) SEQUENCE CHARACTERISTICS:
        ( A ) LENGTH: 8 amino acid residues
        ( B ) TYPE: amino acid
        ( C ) STRANDEDNESS: single ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                    ( A ) ORGANISM: T7 phage
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:4:

Phe   Pro   Asn   Leu   Ala   Gln   Ile   Pro
 1                       5

( 2 ) INFORMATION FOR SEQ ID NO:5:

( i ) SEQUENCE CHARACTERISTICS:
                    ( A ) LENGTH: 8 amino acid residues
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                    ( A ) ORGANISM: Thermus aquaticus
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:

( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:5:

Asp Pro Asn Leu Glu Asn Ile Pro
 1                   5

( 2 ) INFORMATION FOR SEQ ID NO:6:

( i ) SEQUENCE CHARACTERISTICS:
                    ( A ) LENGTH: 8 amino acid residues
                    ( B ) TYPE: amino acid
                    ( C ) STRANDEDNESS: single
                    ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                    ( A ) ORGANISM: Streptococcus pneumoniae
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:

(B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:6:

Asp Pro Asn Leu Glu Asn Ile Pro
 1               5

(2) INFORMATION FOR SEQ ID NO:7:

(i) SEQUENCE CHARACTERISTICS:
            (A) LENGTH: 7 amino acid residues
            (B) TYPE: amino acid
            (C) STRANDEDNESS: single
            (D) TOPOLOGY: linear (ii) MOLECULE TYPE: protein (iii) HYPOTHETICAL:

(iv) ANTI-SENSE:

(v) FRAGMENT TYPE: internal fragment (vi) ORIGINAL SOURCE:
            (A) ORGANISM: Escherichia coli
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:7:

Gln Val His Asp Glu Leu Val
 1               5

(2) INFORMATION FOR SEQ ID NO:8:

```
        ( i ) SEQUENCE CHARACTERISTICS:
                ( A ) LENGTH: 7 amino acid residues
                ( B ) TYPE: amino acid
                ( C ) STRANDEDNESS: single
                ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                ( A ) ORGANISM: T7 phage
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:8:

Trp Val His Asp Glu Ile Gln
 1                   5

( 2 ) INFORMATION FOR SEQ ID NO:9:

( i ) SEQUENCE CHARACTERISTICS:
                ( A ) LENGTH: 7 amino acid residues
                ( B ) TYPE: amino acid
                ( C ) STRANDEDNESS: single
                ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
                ( A ) ORGANISM: Thermus aquaticus
                ( B ) STRAIN:
                ( C ) INDIVIDUAL ISOLATE:
                ( D ) DEVELOPMENTAL STAGE:
```

```
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY:
              ( B ) LOCATION:
              ( C ) IDENTIFICATION METHOD:
              ( D ) OTHER INFORMATION:

( x ) PUBLICATION INFORMATION:
              ( A ) AUTHORS:
              ( B ) TITLE:
              ( C ) JOURNAL:
              ( D ) VOLUME:
              ( E ) ISSUE:
              ( F ) PAGES:
              ( G ) DATE:
              ( H ) DOCUMENT NUMBER:
              ( I ) FILING DATE:
              ( J ) PUBLICATION DATE:
              ( K ) RELEVANT RESIDUES IN SEQ ID NO:

( x i ) SEQUENCE DESCRIPTION: SEQ ID NO:9:

Gln  Val  His  Asp  Glu  Leu  Val
 1                    5
```

( 2 ) INFORMATION FOR SEQ ID NO:10:

```
         ( i ) SEQUENCE CHARACTERISTICS:
              ( A ) LENGTH: 7 amino acid residues
              ( B ) TYPE: amino acid
              ( C ) STRANDEDNESS: single
              ( D ) TOPOLOGY: linear ( i i ) MOLECULE TYPE: protein ( i i i ) HYPOTHETICAL:

( i v ) ANTI-SENSE:

( v ) FRAGMENT TYPE: internal fragment ( v i ) ORIGINAL SOURCE:
              ( A ) ORGANISM: Streptococcus pneumoniae
              ( B ) STRAIN:
              ( C ) INDIVIDUAL ISOLATE:
              ( D ) DEVELOPMENTAL STAGE:
              ( E ) HAPLOTYPE:
              ( F ) TISSUE TYPE:
              ( G ) CELL TYPE:
              ( H ) CELL LINE:
              ( I ) ORGANELLE:

( v i i ) IMMEDIATE SOURCE:
              ( A ) LIBRARY:
              ( B ) CLONE:

( v i i i ) POSITION IN GENOME:
              ( A ) CHROMOSOME/SEGMENT:
              ( B ) MAP POSITION:
              ( C ) UNITS:

( i x ) FEATURE:
              ( A ) NAME/KEY:
              ( B ) LOCATION:
              ( C ) IDENTIFICATION METHOD:
```

(D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:10:

Glu Val His Asp Glu Ile Val
1               5

(2) INFORMATION FOR SEQ ID NO:11:

(i) SEQUENCE CHARACTERISTICS:
        (A) LENGTH: 3252 base pairs
        (B) TYPE: nucleic acid
        (C) STRANDEDNESS: double
        (D) TOPOLOGY: linear (ii) MOLECULE TYPE: genomic DNA (iii) HYPOTHETICAL:

(iv) ANTI-SENSE:

(v) FRAGMENT TYPE:

(vi) ORIGINAL SOURCE:
        (A) ORGANISM: Bacillus caldotenax
        (B) STRAIN: YT-G(DSM406)
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:11:

CCATGGATAT ATTACCGTAG CGAGCAAAGT GGGGCGCGGC ACCGTGTTCA CGATCCATTT    60

-continued

| | | | | | |
|---|---|---|---|---|---|
| TCCAAAGCCG | GGGCGGTAGC | CGGCTTCTTT | TTATCATCTC | CAACTGAGAA | GCCTGCCATT | 120 |
| TTTCAGCGTG | ACGTGAGCAC | GGGATGAATC | CGCGCCTCCC | ATCATGTTGG | GAGAGCGTTC | 180 |
| AAGGCAAGCC | GCAGGCATGG | TACAATAGGA | CAAGGAAGCA | TCCGAGGAGG | GATGAGA | 237 |

```
TTG AAA AAA AAG CTT GTT TTA ATC GAC GGC AGC AGC GTG GCG TAC      282
CGC GCC TTT TTC GCC TTG CCG CTT TTG CAT AAC GAC AAA GGC ATC      327
CAT ACG AAC GCC GTC TAC GGG TTT ACG ATG ATG TTG AAT AAA ATT      372
TTG GCG GAA GAA GAG CCA ACT CAT ATG CTT GTC GCG TTT GAC GCC      417
GGG AAA ACG ACG TTC CGG CAT GAA GCG TTT CAA GAG TAT AAA GGT      462
GGG CGC CAG CAG ACG CCA CCG GAG CTG TCG GAG CAG TTT CCG CTG      507
TTG CGC GAG CTG CTG AGG GCG TAT CGC ATC CCC GCC TAT GAA CTC      552
GAG AAC TAC GAA GCG GAC GAT ATT ATC GGA ACG CTT GCC GCC CGC      597
GCT GAG CAG GAA GGG TTT GAG GTG AAA GTC ATT CCG GGC GAC CGC      642
GAT CTG ACC CAG CTC GCC TCC CCC CAT GTG ACG GTG GAC ATT ACG      687
AAA AAA GGG ATT ACC GAT ATC GAA CCG TAC ACG CCG GAG GCG GTC      732
CGC GAA AAA TAC GGC TTA ACT CCG GAA CAA ATC GTT GAT TTG AAA      777
GGA TTG ATG GGC GAC AAA TCG GAC AAC ATT CCC GGA GTG CCG GGC      822
ATC GGG GAA AAG ACG GCG GTC AAG CTG CTC AGG CAA TTC GGC ACG      867
GTC GAA AAC GTG CTT GCC TCC ATT GAC GAG ATC AAA GGC GAA AAG      912
TTG AAA GAA ACG CTG CGC CAA CAC CGG GAG ATG GCG CTG TTA AGC      957
AAA AAG CTC GCC GCC ATT CGC CGC GAC GCC CCG GTC GAG CTC TCG     1002
CTT GAT GAC ATC GCC TAT CAA GGG GAA GAC CGG GAG AAA GTG GTC     1047
GCT TTA TTT AAA GAG CTT GGG TTT CAA TCG TTT TTA GAG AAA ATG     1092
GAA TCG CCG TCA TCA GAA GAG GAA AAA CCG CTT GCC AAG ATG GCA     1137
TTT ACG CTT GCT GAC CGC GTG ACG GAG GAG ATG CTT GCC GAC AAG     1182
GCG GCG CTT GTC GTT GAA GTG GTC GAG GAA AAT TAT CAT GAT GCG     1227
CCG ATC GTC GGC ATC GCT GTG GTC AAC GAA CAT GGA CGG TTT TTC     1272
CTG CGC CCG GAG ACG GCG CTT GCC GAT CCG CAG TTT GTC GCC TGG     1317
CTT GGT GAT GAA ACG AAG AAA AAA AGC ATG TTT GAC TCA AAG CGC     1362
GCG GCA GTC GCC TTG AAA TGG AAA GGA ATT GAG CTA TGC GGC GTT     1407
TCC TTT GAT TTA TTG CTG GCC GCC TAT TTG CTT GAT CCG GCG CAA     1452
GGT GTT GAT GAT GTG GCT GCC GCA GCA AAA ATG AAG CAA TAC GAA     1497
GCG GTG CGC CCG GAT GAA GCG GTG TAT GGC AAA GGG GCG AAG CGG     1542
GCC GTG CCG GAT GAG CCA GTG CTC GCC GAG CAT TTG GTC CGC AAG     1587
GCG GCG GCG ATT TGG GCG CTC GAA CGG CCG TTT TTG GAT GAG CTG     1632
CGC CGC AAC GAA CAA GAT CGG TTG CTC GTC GAG CTC GAG CAG CCG     1677
TTG TCT TCG ATT TTG GCG GAA ATG GAA TTT GCC GGA GTG AAA GTG     1722
GAT ACG AAG CGG CTC GAA CAG ATG GGC GAA GAG CTC GCC GAG CAG     1767
CTG CGC ACG GTC GAG CAG CGC ATT TAT GAG CTC GCC GGC CAA GAA     1812
TTC AAC ATC AAT TCA CCG AAA CAG CTC GGC GTC ATT TTA TTT GAA     1857
AAA CTG CAG CTG CCC GTC TTG AAA AAA AGC AAA ACC GGC TAC TCC     1902
```

```
ACT TCG GCG GAT GTG CTT GAA AAA CTT GCG CCT TAT CAC GAG ATC        1947
GTG GAA AAC ATT TTG CAA CAT TAC CGC CAG CTT GGC AAG TTG CAG        1992
TCG ACG TAT ATT GAA GGA TTG CTG AAA GTC GTG CGA CCC GAT ACA        2037
AAG AAG GTG CAT ACG ATT TTC AAT CAG GCG TTG ACG CAA ACC GGA        2082
CGG CTC AGC TCG ACG GAG CCG AAC TTG CAA AAC ATT CCG ATT CGG        2127
CTT GAG GAA GGA CGG AAA ATC CGC CAA GCG TTC GTG CCG TCG GAG        2172
TCT GAT TGG CTC ATT TTC GCT GCC GAC TAC TCG CAA ATT GAG TTG        2217
CGC GTC CTC GCC CAT ATT GCG GAA GAT GAC AAT TTA ATG GAA GCG        2262
TTC CGC CGC GAT TTG GAT ATC CAT ACG AAA ACA GCG ATG GAC ATT        2307
TTC CAA GTG AGC GAG GAC GAA GTG ACG CCC AAC ATG CGC CGT CAG        2352
GCG AAG GCG GTC AAC TTT GGG ATC GTT TAC GGG ATC AGT GAT TAC        2397
GGC TTG GCG CAA AAC TTA AAT ATT TCA CGC AAA GAG GCC GCT GAA        2442
TTC ATC GAG CGC TAC TTC GAA AGC TTC CCT GGC GTG AAG CGG TAT        2487
ATG GAA AAC ATT GTG CAA GAA GCA AAA CAG AAA GGG TAT GTG ACG        2532
ACG CTG CTG CAT CGG CGC CGC TAT TTG CCG GAT ATT ACG AGC CGC        2577
AAC TTC AAC GTC CGC AGC TTT GCT GAA CGG ATG GCG ATG AAC ACG        2622
CCG ATT CAA GGG AGC GCC GCT GAC ATT ATT AAA AAG GCG ATG ATC        2667
GAT CTG AAC GCC AGA CTG AAG GAA GAG CGG CTG CAA GCG CGC CTT        2712
TTG CTG CAG GTG CAT GAC GAG CTC ATT TTG GAG GCG CCG AAA GAA        2757
GAG ATG GAG CGG CTG TGC CGG CTC GTT CCG GAA GTG ATG GAG CAA        2802
GCG GTC ACA CTT CGC GTG CCG CTC AAA GTC GAT TAC CAT TAC GGC        2847
TCG ACA TGG TAT GAC GCG AAA TAAAAGGAG TCTTGGTGTG TGGATCGCCG        2898
GCACCCCTAA AAGGCCGGTG ATTTAAGGGG AAATACTGCT CTCCAACAGT GTTTCTCAAA  2958
TTGAAAAACC TTGCAACACC ATCACTTCAT TCCTTGTGAT TTCTCATAAA TCAAGCGAAT  3018
CCATTGTTTT TCATCAGCCT TCTAAGAAGG CCTGTGATGG AATGAAAAAG CAGTTTCACA  3078
ACGACTCTTC TCCAGTTGAG AAGCCTTGGG ACATCGAGTC GTCCTTCTCA ACCAACATGA  3138
CCGATTTTGC GAAAATCAGC GTTTCTCACC GGCCTTCTAG GCAGAATCTT TCGGTGCGAC  3198
GATTCTCGGC TGCAACTCGG ATGAATTGGA GCGAAATCAG CTGCCGCCCC ATGG        3252
```

( 2 ) INFORMATION FOR SEQ ID NO:12:

( i ) SEQUENCE CHARACTERISTICS:
        ( A ) LENGTH: 22 amino acid residues
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE: N-terminal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:

( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:12:

```
Met Lys Lys Lys Leu Val Leu Ile Asp Gly Ser Ser Val Ala Tyr
 1               5                   1 0                  1 5

Arg Ala Phe Phe Ala Leu Pro
                2 0
```

( 2 ) INFORMATION FOR SEQ ID NO:13:

( i ) SEQUENCE CHARACTERISTICS:
            ( A ) LENGTH: 2631 base pairs
            ( B ) TYPE: nucleic acid
            ( C ) STRANDEDNESS: double
            ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
            ( A ) ORGANISM: Bacillus caldotenax
            ( B ) STRAIN: YT-G(DSM406)
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:

( C ) IDENTIFICATION METHOD:
( D ) OTHER INFORMATION:

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:13:

| | | | | | | | | | | | | | | | |
|---|---|---|---|---|---|---|---|---|---|---|---|---|---|---|---|
| TTG | AAA | AAA | AAG | CTT | GTT | TTA | ATC | GAC | GGC | AGC | AGC | GTG | GCG | TAC | 45 |
| CGC | GCC | TTT | TTC | GCC | TTG | CCG | CTT | TTG | CAT | AAC | GAC | AAA | GGC | ATC | 90 |
| CAT | ACG | AAC | GCC | GTC | TAC | GGG | TTT | ACG | ATG | ATG | TTG | AAT | AAA | ATT | 135 |
| TTG | GCG | GAA | GAA | GAG | CCA | ACT | CAT | ATG | CTT | GTC | GCG | TTT | GAC | GCC | 180 |
| GGG | AAA | ACG | ACG | TTC | CGG | CAT | GAA | GCG | TTT | CAA | GAG | TAT | AAA | GGT | 225 |
| GGG | CGC | CAG | CAG | ACG | CCA | CCG | GAG | CTG | TCG | GAG | CAG | TTT | CCG | CTG | 270 |
| TTG | CGC | GAG | CTG | CTG | AGG | GCG | TAT | CGC | ATC | CCC | GCC | TAT | GAA | CTC | 315 |
| GAG | AAC | TAC | GAA | GCG | GAC | GAT | ATT | ATC | GGA | ACG | CTT | GCC | GCC | CGC | 360 |
| GCT | GAG | CAG | GAA | GGG | TTT | GAG | GTG | AAA | GTC | ATT | TCC | GGC | GAC | CGC | 405 |
| GAT | CTG | ACC | CAG | CTC | GCC | TCC | CCC | CAT | GTG | ACG | GTG | GAC | ATT | ACG | 450 |
| AAA | AAA | GGG | ATT | ACC | GAT | ATC | GAA | CCG | TAC | ACG | CCG | GAG | GCG | GTC | 495 |
| CGC | GAA | AAA | TAC | GGC | TTA | ACT | CCG | GAA | CAA | ATC | GTT | GAT | TTG | AAA | 540 |
| GGA | TTG | ATG | GGC | GAC | AAA | TCG | GAC | AAC | ATT | CCC | GGA | GTG | CCG | GGC | 585 |
| ATC | GGG | GAA | AAG | ACG | GCG | GTC | AAG | CTG | CTC | AGG | CAA | TTC | GGC | ACG | 630 |
| GTC | GAA | AAC | GTG | CTT | GCC | TCC | ATT | GAC | GAG | ATC | AAA | GGC | GAA | AAG | 675 |
| TTG | AAA | GAA | ACG | CTG | CGC | CAA | CAC | CGG | GAG | ATG | GCG | CTG | TTA | AGC | 720 |
| AAA | AAG | CTC | GCC | GCC | ATT | CGC | CGC | GAC | GCC | CCG | GTC | GAG | CTC | TCG | 765 |
| CTT | GAT | GAC | ATC | GCC | TAT | CAA | GGG | GAA | GAC | CGG | GAG | AAA | GTG | GTC | 810 |
| GCT | TTA | TTT | AAA | GAG | CTT | GGG | TTT | CAA | TCG | TTT | TTA | GAG | AAA | ATG | 855 |
| GAA | TCG | CCG | TCA | TCA | GAA | GAG | GAA | AAA | CCG | CTT | GCC | AAG | ATG | GCA | 900 |
| TTT | ACG | CTT | GCT | GAC | CGC | GTG | ACG | GAG | GAG | ATG | CTT | GCC | GAC | AAG | 945 |
| GCG | GCG | CTT | GTC | GTT | GAA | GTG | GTC | GAG | GAA | AAT | TAT | CAT | GAT | GCG | 990 |
| CCG | ATC | GTC | GGC | ATC | GCT | GTG | GTC | AAC | GAA | CAT | GGA | CGG | TTT | TTC | 1035 |
| CTG | CGC | CCG | GAG | ACG | GCG | CTT | GCC | GAT | CCG | CAG | TTT | GTC | GCC | TGG | 1080 |
| CTT | GGT | GAT | GAA | ACG | AAG | AAA | AAA | AGC | ATG | TTT | GAC | TCA | AAG | CGC | 1125 |
| GCG | GCA | GTC | GCC | TTG | AAA | TGG | AAA | GGA | ATT | GAG | CTA | TGC | GGC | GTT | 1170 |
| TCC | TTT | GAT | TTA | TTG | CTG | GCC | GCC | TAT | TTG | CTT | GAT | CCG | GCG | CAA | 1215 |
| GGT | GTT | GAT | GAT | GTG | GCT | GCC | GCA | GCA | AAA | ATG | AAG | CAA | TAC | GAA | 1260 |
| GCG | GTG | CGC | CCG | GAT | GAA | GCG | GTG | TAT | GGC | AAA | GGG | GCG | AAG | CGG | 1305 |
| GCC | GTG | CCG | GAT | GAG | CCA | GTG | CTC | GCC | GAG | CAT | TTG | GTC | CGC | AAG | 1350 |
| GCG | GCG | GCG | ATT | TGG | GCG | CTC | GAA | CGG | CCG | TTT | TTG | GAT | GAG | CTG | 1395 |

|     |     |     |     |     |     |     |     |     |     |     |     |     |     |     |      |
|-----|-----|-----|-----|-----|-----|-----|-----|-----|-----|-----|-----|-----|-----|-----|------|
| CGC | CGC | AAC | GAA | CAA | GAT | CGG | TTG | CTC | GTC | GAG | CTC | GAG | CAG | CCG | 1440 |
| TTG | TCT | TCG | ATT | TTG | GCG | GAA | ATG | GAA | TTT | GCC | GGA | GTG | AAA | GTG | 1485 |
| GAT | ACG | AAG | CGG | CTC | GAA | CAG | ATG | GGC | GAA | GAG | CTC | GCC | GAG | CAG | 1530 |
| CTG | CGC | ACG | GTC | GAG | CAG | CGC | ATT | TAT | GAG | CTC | GCC | GGC | CAA | GAA | 1575 |
| TTC | AAC | ATC | AAT | TCA | CCG | AAA | CAG | CTC | GGC | GTC | ATT | TTA | TTT | GAA | 1620 |
| AAA | CTG | CAG | CTG | CCC | GTC | TTG | AAA | AAA | AGC | AAA | ACC | GGC | TAC | TCC | 1665 |
| ACT | TCG | GCG | GAT | GTG | CTT | GAA | AAA | CTT | GCG | CCT | TAT | CAC | GAG | ATC | 1710 |
| GTG | GAA | AAC | ATT | TTG | CAA | CAT | TAC | CGC | CAG | CTT | GGC | AAG | TTG | CAG | 1755 |
| TCG | ACG | TAT | ATT | GAA | GGA | TTG | CTG | AAA | GTC | GTG | CGA | CCC | GAT | ACA | 1800 |
| AAG | AAG | GTG | CAT | ACG | ATT | TTC | AAT | CAG | GCG | TTG | ACG | CAA | ACC | GGA | 1845 |
| CGG | CTC | AGC | TCG | ACG | GAG | CCG | AAC | TTG | CAA | AAC | ATT | CCG | ATT | CGG | 1890 |
| CTT | GAG | GAA | GGA | CGG | AAA | ATC | CGC | CAA | GCG | TTC | GTG | CCG | TCG | GAG | 1935 |
| TCT | GAT | TGG | CTC | ATT | TTC | GCT | GCC | GAC | TAC | TCG | CAA | ATT | GAG | TTG | 1980 |
| CGC | GTC | CTC | GCC | CAT | ATT | GCG | GAA | GAT | GAC | AAT | TTA | ATG | GAA | GCG | 2025 |
| TTC | CGC | CGC | GAT | TTG | GAT | ATC | CAT | ACG | AAA | ACA | GCG | ATG | GAC | ATT | 2070 |
| TTC | CAA | GTG | AGC | GAG | GAC | GAA | GTG | ACG | CCC | AAC | ATG | CGC | CGT | CAG | 2115 |
| GCG | AAG | GCG | GTC | AAC | TTT | GGG | ATC | GTT | TAC | GGG | ATC | AGT | GAT | TAC | 2160 |
| GGC | TTG | GCG | CAA | AAC | TTA | AAT | ATT | TCA | CGC | AAA | GAG | GCC | GCT | GAA | 2205 |
| TTC | ATC | GAG | CGC | TAC | TTC | GAA | AGC | TTC | CCT | GGC | GTG | AAG | CGG | TAT | 2250 |
| ATG | GAA | AAC | ATT | GTG | CAA | GAA | GCA | AAA | CAG | AAA | GGG | TAT | GTG | ACG | 2295 |
| ACG | CTG | CTG | CAT | CGG | CGC | CGC | TAT | TTG | CCG | GAT | ATT | ACG | AGC | CGC | 2340 |
| AAC | TTC | AAC | GTC | CGC | AGC | TTT | GCT | GAA | CGG | ATG | GCG | ATG | AAC | ACG | 2385 |
| CCG | ATT | CAA | GGG | AGC | GCC | GCT | GAC | ATT | ATT | AAA | AAG | GCG | ATG | ATC | 2430 |
| GAT | CTG | AAC | GCC | AGA | CTG | AAG | GAA | GAG | CGG | CTG | CAA | GCG | CGC | CTT | 2475 |
| TTG | CTG | CAG | GTG | CAT | GAC | GAG | CTC | ATT | TTG | GAG | GCG | CCG | AAA | GAA | 2520 |
| GAG | ATG | GAG | CGG | CTG | TGC | CGG | CTC | GTT | CCG | GAA | GTG | ATG | GAG | CAA | 2565 |
| GCG | GTC | ACA | CTT | CGC | GTG | CCG | CTC | AAA | GTC | GAT | TAC | CAT | TAC | GGC | 2610 |
| TCG | ACA | TGG | TAT | GAC | GCG | AAA |     |     |     |     |     |     |     |     | 2631 |

( 2 ) INFORMATION FOR SEQ ID NO:14:

( i ) SEQUENCE CHARACTERISTICS:
        ( A ) LENGTH: 877 amino acid residues
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:

( G ) CELL TYPE:
( H ) CELL LINE:
( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY:
    ( B ) LOCATION:
    ( C ) IDENTIFICATION METHOD:
    ( D ) OTHER INFORMATION:

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:14:

```
Met Lys Lys Lys Leu Val Leu Ile Asp Gly Ser Ser Val Ala Tyr
 1               5                  10                  15

Arg Ala Phe Phe Ala Leu Pro Leu Leu His Asn Asp Lys Gly Ile
                20                  25                  30

His Thr Asn Ala Val Tyr Gly Phe Thr Met Met Leu Asn Lys Ile
                35                  40                  45

Leu Ala Glu Glu Glu Pro Thr His Met Leu Val Ala Phe Asp Ala
                50                  55                  60

Gly Lys Thr Thr Phe Arg His Glu Ala Phe Gln Glu Tyr Lys Gly
                65                  70                  75

Gly Arg Gln Gln Thr Pro Pro Glu Leu Ser Glu Gln Phe Pro Leu
                80                  85                  90

Leu Arg Glu Leu Leu Arg Ala Tyr Arg Ile Pro Ala Tyr Glu Leu
                95                  100                 105

Glu Asn Tyr Glu Ala Asp Asp Ile Ile Gly Thr Leu Ala Ala Arg
                110                 115                 120

Ala Glu Gln Glu Gly Phe Glu Val Lys Val Ile Ser Gly Asp Arg
                125                 130                 135

Asp Leu Thr Gln Leu Ala Ser Pro His Val Thr Val Asp Ile Thr
                140                 145                 150

Lys Lys Gly Ile Thr Asp Ile Glu Pro Tyr Thr Pro Glu Ala Val
                155                 160                 165

Arg Glu Lys Tyr Gly Leu Thr Pro Glu Gln Ile Val Asp Leu Lys
                170                 175                 180

Gly Leu Met Gly Asp Lys Ser Asp Asn Ile Pro Gly Val Pro Gly
                185                 190                 195

Ile Gly Glu Lys Thr Ala Val Lys Leu Leu Arg Gln Phe Gly Thr
                200                 205                 210

Val Glu Asn Val Leu Ala Ser Ile Asp Glu Ile Lys Gly Glu Lys
                215                 220                 225

Leu Lys Glu Thr Leu Arg Gln His Arg Glu Met Ala Leu Leu Ser
```

-continued

|     |     |     |     | 230 |     |     |     |     | 235 |     |     |     |     | 240 |
|---|---|---|---|---|---|---|---|---|---|---|---|---|---|---|
| Lys | Lys | Leu | Ala | Ala | Ile | Arg | Arg | Asp | Ala | Pro | Val | Glu | Leu | Ser |
|     |     |     |     | 245 |     |     |     |     | 250 |     |     |     |     | 255 |
| Leu | Asp | Asp | Ile | Ala | Tyr | Gln | Gly | Glu | Asp | Arg | Glu | Lys | Val | Val |
|     |     |     |     | 260 |     |     |     |     | 265 |     |     |     |     | 270 |
| Ala | Leu | Phe | Lys | Glu | Leu | Gly | Phe | Gln | Ser | Phe | Leu | Glu | Lys | Met |
|     |     |     |     | 275 |     |     |     |     | 280 |     |     |     |     | 285 |
| Glu | Ser | Pro | Ser | Ser | Glu | Glu | Glu | Lys | Pro | Leu | Ala | Lys | Met | Ala |
|     |     |     |     | 290 |     |     |     |     | 295 |     |     |     |     | 300 |
| Phe | Thr | Leu | Ala | Asp | Arg | Val | Thr | Glu | Met | Leu | Ala | Asp | Lys |     |
|     |     |     |     | 305 |     |     |     |     | 310 |     |     |     |     | 315 |
| Ala | Ala | Leu | Val | Val | Glu | Val | Val | Glu | Glu | Asn | Tyr | His | Asp | Ala |
|     |     |     |     | 320 |     |     |     |     | 325 |     |     |     |     | 330 |
| Pro | Ile | Val | Gly | Ile | Ala | Val | Val | Asn | Glu | His | Gly | Arg | Phe | Phe |
|     |     |     |     | 335 |     |     |     |     | 340 |     |     |     |     | 345 |
| Leu | Arg | Pro | Glu | Thr | Ala | Leu | Ala | Asp | Pro | Gln | Phe | Val | Ala | Trp |
|     |     |     |     | 350 |     |     |     |     | 355 |     |     |     |     | 360 |
| Leu | Gly | Asp | Glu | Thr | Lys | Lys | Lys | Ser | Met | Phe | Asp | Ser | Lys | Arg |
|     |     |     |     | 365 |     |     |     |     | 370 |     |     |     |     | 375 |
| Ala | Ala | Val | Ala | Leu | Lys | Trp | Lys | Gly | Ile | Glu | Leu | Cys | Gly | Val |
|     |     |     |     | 380 |     |     |     |     | 385 |     |     |     |     | 390 |
| Ser | Phe | Asp | Leu | Leu | Leu | Ala | Ala | Tyr | Leu | Leu | Asp | Pro | Ala | Gln |
|     |     |     |     | 395 |     |     |     |     | 400 |     |     |     |     | 405 |
| Gly | Val | Asp | Asp | Val | Ala | Ala | Ala | Ala | Lys | Met | Lys | Gln | Tyr | Glu |
|     |     |     |     | 410 |     |     |     |     | 415 |     |     |     |     | 420 |
| Ala | Val | Arg | Pro | Asp | Glu | Ala | Val | Tyr | Gly | Lys | Gly | Ala | Lys | Arg |
|     |     |     |     | 425 |     |     |     |     | 430 |     |     |     |     | 435 |
| Ala | Val | Pro | Asp | Glu | Pro | Val | Leu | Ala | Glu | His | Leu | Val | Arg | Lys |
|     |     |     |     | 440 |     |     |     |     | 445 |     |     |     |     | 450 |
| Ala | Ala | Ala | Ile | Trp | Ala | Leu | Glu | Arg | Pro | Phe | Leu | Asp | Glu | Leu |
|     |     |     |     | 455 |     |     |     |     | 460 |     |     |     |     | 465 |
| Arg | Arg | Asn | Glu | Gln | Asp | Arg | Leu | Leu | Val | Glu | Leu | Glu | Gln | Pro |
|     |     |     |     | 470 |     |     |     |     | 475 |     |     |     |     | 480 |
| Leu | Ser | Ser | Ile | Leu | Ala | Glu | Met | Glu | Phe | Ala | Gly | Val | Lys | Val |
|     |     |     |     | 485 |     |     |     |     | 490 |     |     |     |     | 495 |
| Asp | Thr | Lys | Arg | Leu | Glu | Gln | Met | Gly | Glu | Glu | Leu | Ala | Glu | Gln |
|     |     |     |     | 500 |     |     |     |     | 505 |     |     |     |     | 510 |
| Leu | Arg | Thr | Val | Glu | Gln | Arg | Ile | Tyr | Glu | Leu | Ala | Gly | Gln | Glu |
|     |     |     |     | 515 |     |     |     |     | 520 |     |     |     |     | 525 |
| Phe | Asn | Ile | Asn | Ser | Pro | Lys | Gln | Leu | Gly | Val | Ile | Leu | Phe | Glu |
|     |     |     |     | 530 |     |     |     |     | 535 |     |     |     |     | 540 |
| Lys | Leu | Gln | Leu | Pro | Val | Leu | Lys | Lys | Ser | Lys | Thr | Gly | Tyr | Ser |
|     |     |     |     | 545 |     |     |     |     | 550 |     |     |     |     | 555 |
| Thr | Ser | Ala | Asp | Val | Leu | Glu | Lys | Leu | Ala | Pro | Tyr | His | Glu | Ile |
|     |     |     |     | 560 |     |     |     |     | 565 |     |     |     |     | 570 |
| Val | Glu | Asn | Ile | Leu | Gln | His | Tyr | Arg | Gln | Leu | Gly | Lys | Leu | Gln |
|     |     |     |     | 575 |     |     |     |     | 580 |     |     |     |     | 585 |
| Ser | Thr | Tyr | Ile | Glu | Gly | Leu | Leu | Lys | Val | Val | Arg | Pro | Asp | Thr |
|     |     |     |     | 590 |     |     |     |     | 595 |     |     |     |     | 600 |
| Lys | Lys | Val | His | Thr | Ile | Phe | Asn | Gln | Ala | Leu | Thr | Gln | Thr | Gly |
|     |     |     |     | 605 |     |     |     |     | 610 |     |     |     |     | 615 |
| Arg | Leu | Ser | Ser | Thr | Glu | Pro | Asn | Leu | Gln | Asn | Ile | Pro | Ile | Arg |
|     |     |     |     | 620 |     |     |     |     | 625 |     |     |     |     | 630 |

| | | | | | | | | | | | | | | |
|---|---|---|---|---|---|---|---|---|---|---|---|---|---|---|
| Leu | Glu | Glu | Gly | Arg<br>635 | Lys | Ile | Arg | Gln | Ala<br>640 | Phe | Val | Pro | Ser | Glu<br>645 |
| Ser | Asp | Trp | Leu | Ile<br>650 | Phe | Ala | Ala | Asp | Tyr<br>655 | Ser | Gln | Ile | Glu | Leu<br>660 |
| Arg | Val | Leu | Ala | His<br>665 | Ile | Ala | Glu | Asp | Asp<br>670 | Asn | Leu | Met | Glu | Ala<br>675 |
| Phe | Arg | Arg | Asp | Leu<br>680 | Asp | Ile | His | Thr | Lys<br>685 | Thr | Ala | Met | Asp | Ile<br>690 |
| Phe | Gln | Val | Ser | Glu<br>695 | Asp | Glu | Val | Thr | Pro<br>700 | Asn | Met | Arg | Arg | Gln<br>705 |
| Ala | Lys | Ala | Val | Asn<br>710 | Phe | Gly | Ile | Val | Tyr<br>715 | Gly | Ile | Ser | Asp | Tyr<br>720 |
| Gly | Leu | Ala | Gln | Asn<br>725 | Leu | Asn | Ile | Ser | Arg<br>730 | Lys | Glu | Ala | Ala | Glu<br>735 |
| Phe | Ile | Glu | Arg | Tyr<br>740 | Phe | Glu | Ser | Phe | Pro<br>745 | Gly | Val | Lys | Arg | Tyr<br>750 |
| Met | Glu | Asn | Ile | Val<br>755 | Gln | Glu | Ala | Lys | Gln<br>760 | Lys | Gly | Tyr | Val | Thr<br>765 |
| Thr | Leu | Leu | His | Arg<br>770 | Arg | Arg | Tyr | Leu | Pro<br>775 | Asp | Ile | Thr | Ser | Arg<br>780 |
| Asn | Phe | Asn | Val | Arg<br>785 | Ser | Phe | Ala | Glu | Arg<br>790 | Met | Ala | Met | Asn | Thr<br>795 |
| Pro | Ile | Gln | Gly | Ser<br>800 | Ala | Ala | Asp | Ile | Ile<br>805 | Lys | Lys | Ala | Met | Ile<br>810 |
| Asp | Leu | Asn | Ala | Arg<br>815 | Leu | Lys | Glu | Glu | Arg<br>820 | Leu | Gln | Ala | Arg | Leu<br>825 |
| Leu | Leu | Gln | Val | His<br>830 | Asp | Glu | Leu | Ile | Leu<br>835 | Glu | Ala | Pro | Lys | Glu<br>840 |
| Glu | Met | Glu | Arg | Leu<br>845 | Cys | Arg | Leu | Val | Pro<br>850 | Glu | Val | Met | Glu | Gln<br>855 |
| Ala | Val | Thr | Leu | Arg<br>860 | Val | Pro | Leu | Lys | Val<br>865 | Asp | Tyr | His | Tyr | Gly<br>870 |
| Ser | Thr | Trp | Tyr | Asp<br>875 | Ala | Lys | | | | | | | | |

( 2 ) INFORMATION FOR SEQ ID NO:15:

( i ) SEQUENCE CHARACTERISTICS:
        ( A ) LENGTH: 10 amino acid residues
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE: N-terminal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:15:

Met  Glu  Ser  Pro  Ser  Ser  Glu  Glu  Glu  Lys
 1                    5                        1 0

( 2 ) INFORMATION FOR SEQ ID NO:16:

( i ) SEQUENCE CHARACTERISTICS:
                    ( A ) LENGTH: 1779 base pairs
                    ( B ) TYPE: nucleic acid
                    ( C ) STRANDEDNESS: double
                    ( D ) TOPOLOGY: linear ( i i ) MOLECULE TYPE: genomic DNA ( i i i ) HYPOTHETICAL:

( i v ) ANTI-SENSE:

( v ) FRAGMENT TYPE:

( v i ) ORIGINAL SOURCE:
                    ( A ) ORGANISM: Bacillus caldotenax
                    ( B ) STRAIN: YT-G(DSM406)
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY:
                    ( B ) LOCATION:
                    ( C ) IDENTIFICATION METHOD:
                    ( D ) OTHER INFORMATION:

( x ) PUBLICATION INFORMATION:
                    ( A ) AUTHORS:
                    ( B ) TITLE:
                    ( C ) JOURNAL:
                    ( D ) VOLUME:

( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:16:

| | | | | | | | | | | | | | | | |
|---|---|---|---|---|---|---|---|---|---|---|---|---|---|---|---|
| ATG | GAA | TCG | CCG | TCA | TCA | GAA | GAG | GAA | AAA | CCG | CTT | GCC | AAG | ATG | 45 |
| GCA | TTT | ACG | CTT | GCT | GAC | CGC | GTG | ACG | GAG | GAG | ATG | CTT | GCC | GAC | 90 |
| AAG | GCG | GCG | CTT | GTC | GTT | GAA | GTG | GTC | GAG | GAA | AAT | TAT | CAT | GAT | 135 |
| GCG | CCG | ATC | GTC | GGC | ATC | GCT | GTG | GTC | AAC | GAA | CAT | GGA | CGG | TTT | 180 |
| TTC | CTG | CGC | CCG | GAG | ACG | GCG | CTT | GCC | GAT | CCG | CAG | TTT | GTC | GCC | 225 |
| TGG | CTT | GGT | GAT | GAA | ACG | AAG | AAA | AAA | AGC | ATG | TTT | GAC | TCA | AAG | 270 |
| CGC | GCG | GCA | GTC | GCC | TTG | AAA | TGG | AAA | GGA | ATT | GAG | CTA | TGC | GGC | 315 |
| GTT | TCC | TTT | GAT | TTA | TTG | CTG | GCC | GCC | TAT | TTG | CTT | GAT | CCG | GCG | 360 |
| CAA | GGT | GTT | GAT | GAT | GTG | GCT | GCC | GCA | GCA | AAA | ATG | AAG | CAA | TAC | 405 |
| GAA | GCG | GTG | CGC | CCG | GAT | GAA | GCG | GTG | TAT | GGC | AAA | GGG | GCG | AAG | 450 |
| CGG | GCC | GTG | CCG | GAT | GAG | CCA | GTG | CTC | GCC | GAG | CAT | TTG | GTC | CGC | 495 |
| AAG | GCG | GCG | GCG | ATT | TGG | GCG | CTC | GAA | CGG | CCG | TTT | TTG | GAT | GAG | 540 |
| CTG | CGC | CGC | AAC | GAA | CAA | GAT | CGG | TTG | CTC | GTC | GAG | CTC | GAG | CAG | 585 |
| CCG | TTG | TCT | TCG | ATT | TTG | GCG | GAA | ATG | GAA | TTT | GCC | GGA | GTG | AAA | 630 |
| GTG | GAT | ACG | AAG | CGG | CTC | GAA | CAG | ATG | GGC | GAA | GAG | CTC | GCC | GAG | 675 |
| CAG | CTG | CGC | ACG | GTC | GAG | CAG | CGC | ATT | TAT | GAG | CTC | GCC | GGC | CAA | 720 |
| GAA | TTC | AAC | ATC | AAT | TCA | CCG | AAA | CAG | CTC | GGC | GTC | ATT | TTA | TTT | 765 |
| GAA | AAA | CTG | CAG | CTG | CCC | GTC | TTG | AAA | AAA | AGC | AAA | ACC | GGC | TAC | 810 |
| TCC | ACT | TCG | GCG | GAT | GTG | CTT | GAA | AAA | CTT | GCG | CCT | TAT | CAC | GAG | 855 |
| ATC | GTG | GAA | AAC | ATT | TTG | CAA | CAT | TAC | CGC | CAG | CTT | GGC | AAG | TTG | 900 |
| CAG | TCG | ACG | TAT | ATT | GAA | GGA | TTG | CTG | AAA | GTC | GTG | CGA | CCC | GAT | 945 |
| ACA | AAG | AAG | GTG | CAT | ACG | ATT | TTC | AAT | CAG | GCG | TTG | ACG | CAA | ACC | 990 |
| GGA | CGG | CTC | AGC | TCG | ACG | GAG | CCG | AAC | TTG | CAA | AAC | ATT | CCG | ATT | 1035 |
| CGG | CTT | GAG | GAA | GGA | CGG | AAA | ATC | CGC | CAA | GCG | TTC | GTG | CCG | TCG | 1080 |
| GAG | TCT | GAT | TGG | CTC | ATT | TTC | GCT | GCC | GAC | TAC | TCG | CAA | ATT | GAG | 1125 |
| TTG | CGC | GTC | CTC | GCC | CAT | ATT | GCG | GAA | GAT | GAC | AAT | TTA | ATG | GAA | 1170 |
| GCG | TTC | CGC | CGC | GAT | TTG | GAT | ATC | CAT | ACG | AAA | ACA | GCG | ATG | GAC | 1215 |
| ATT | TTC | CAA | GTG | AGC | GAG | GAC | GAA | GTG | ACG | CCC | AAC | ATG | CGC | CGT | 1260 |
| CAG | GCG | AAG | GCG | GTC | AAC | TTT | GGG | ATC | GTT | TAC | GGG | ATC | AGT | GAT | 1305 |
| TAC | GGC | TTG | GCG | CAA | AAC | TTA | AAT | ATT | TCA | CGC | AAA | GAG | GCC | GCT | 1350 |
| GAA | TTC | ATC | GAG | CGC | TAC | TTC | GAA | AGC | TTC | CCT | GGC | GTG | AAG | CGG | 1395 |
| TAT | ATG | GAA | AAC | ATT | GTG | CAA | GAA | GCA | AAA | CAG | AAA | GGG | TAT | GTG | 1440 |
| ACG | ACG | CTG | CTG | CAT | CGG | CGC | CGC | TAT | TTG | CCG | GAT | ATT | ACG | AGC | 1485 |
| CGC | AAC | TTC | AAC | GTC | CGC | AGC | TTT | GCT | GAA | CGG | ATG | GCG | ATG | AAC | 1530 |
| ACG | CCG | ATT | CAA | GGG | AGC | GCC | GCT | GAC | ATT | ATT | AAA | AAG | GCG | ATG | 1575 |

| | | | | | | | | | | | | | | |
|---|---|---|---|---|---|---|---|---|---|---|---|---|---|---|
| ATC | GAT | CTG | AAC | GCC | AGA | CTG | AAG | GAA | GAG | CGG | CTG | CAA | GCG | CGC | 1620 |
| CTT | TTG | CTG | CAG | GTG | CAT | GAC | GAG | CTC | ATT | TTG | GAG | GCG | CCG | AAA | 1665 |
| GAA | GAG | ATG | GAG | CGG | CTG | TGC | CGG | CTC | GTT | CCG | GAA | GTG | ATG | GAG | 1710 |
| CAA | GCG | GTC | ACA | CTT | CGC | GTG | CCG | CTC | AAA | GTC | GAT | TAC | CAT | TAC | 1755 |
| GGC | TCG | ACA | TGG | TAT | GAC | GCG | AAA | | | | | | | | 1779 |

( 2 ) INFORMATION FOR SEQ ID NO:17:

( i ) SEQUENCE CHARACTERISTICS:
        ( A ) LENGTH: 593 amino acid residues
        ( B ) TYPE: amino acid
        ( C ) STRANDEDNESS: single
        ( D ) TOPOLOGY: linear ( i i ) MOLECULE TYPE: protein ( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:17:

| | | | | | | | | | | | | | | |
|---|---|---|---|---|---|---|---|---|---|---|---|---|---|---|
| Met | Glu | Ser | Pro | Ser | Ser | Glu | Glu | Glu | Lys | Pro | Leu | Ala | Lys | Met |
| 1 | | | | 5 | | | | | 10 | | | | | 15 |
| Ala | Phe | Thr | Leu | Ala | Asp | Arg | Val | Thr | Glu | Glu | Met | Leu | Ala | Asp |
| | | | | 20 | | | | | 25 | | | | | 30 |
| Lys | Ala | Ala | Leu | Val | Val | Glu | Val | Val | Glu | Glu | Asn | Tyr | His | Asp |
| | | | | 35 | | | | | 40 | | | | | 45 |
| Ala | Pro | Ile | Val | Gly | Ile | Ala | Val | Val | Asn | Glu | His | Gly | Arg | Phe |
| | | | | 50 | | | | | 55 | | | | | 60 |

-continued

| | | | | | | | | | | | | | |
|---|---|---|---|---|---|---|---|---|---|---|---|---|---|
| Phe | Leu | Arg | Pro | Glu 65 | Thr | Ala | Leu | Ala | Asp 70 | Pro | Gln | Phe | Val | Ala 75 |
| Trp | Leu | Gly | Asp | Glu 80 | Thr | Lys | Lys | Lys | Ser 85 | Met | Phe | Asp | Ser | Lys 90 |
| Arg | Ala | Ala | Val | Ala 95 | Leu | Lys | Trp | Lys | Gly 100 | Ile | Glu | Leu | Cys | Gly 105 |
| Val | Ser | Phe | Asp | Leu 110 | Leu | Leu | Ala | Ala | Tyr 115 | Leu | Leu | Asp | Pro | Ala 120 |
| Gln | Gly | Val | Asp | Asp 125 | Val | Ala | Ala | Ala | Ala 130 | Lys | Met | Lys | Gln | Tyr 135 |
| Glu | Ala | Val | Arg | Pro 140 | Asp | Glu | Ala | Val | Tyr 145 | Gly | Lys | Gly | Ala | Lys 150 |
| Arg | Ala | Val | Pro | Asp 155 | Glu | Pro | Val | Leu | Ala 160 | Glu | His | Leu | Val | Arg 165 |
| Lys | Ala | Ala | Ala | Ile 170 | Trp | Ala | Leu | Glu | Arg 175 | Pro | Phe | Leu | Asp | Glu 180 |
| Leu | Arg | Arg | Asn | Glu 185 | Gln | Asp | Arg | Leu | Leu 190 | Val | Glu | Leu | Glu | Gln 195 |
| Pro | Leu | Ser | Ser | Ile 200 | Leu | Ala | Glu | Met | Glu 205 | Phe | Ala | Gly | Val | Lys 210 |
| Val | Asp | Thr | Lys | Arg 215 | Leu | Glu | Gln | Met | Gly 220 | Glu | Glu | Leu | Ala | Glu 225 |
| Gln | Leu | Arg | Thr | Val 230 | Glu | Gln | Arg | Ile | Tyr 235 | Glu | Leu | Ala | Gly | Gln 240 |
| Glu | Phe | Asn | Ile | Asn 245 | Ser | Pro | Lys | Gln | Leu 250 | Gly | Val | Ile | Leu | Phe 255 |
| Glu | Lys | Leu | Gln | Leu 260 | Pro | Val | Leu | Lys | Lys 265 | Ser | Lys | Thr | Gly | Tyr 270 |
| Ser | Thr | Ser | Ala | Asp 275 | Val | Leu | Glu | Lys | Leu 280 | Ala | Pro | Tyr | His | Glu 285 |
| Ile | Val | Glu | Asn | Ile 290 | Leu | Gln | His | Tyr | Arg 295 | Gln | Leu | Gly | Lys | Leu 300 |
| Gln | Ser | Thr | Tyr | Ile 305 | Glu | Gly | Leu | Leu | Lys 310 | Val | Val | Arg | Pro | Asp 315 |
| Thr | Lys | Lys | Val | His 320 | Thr | Ile | Phe | Asn | Gln 325 | Ala | Leu | Thr | Gln | Thr 330 |
| Gly | Arg | Leu | Ser | Ser 335 | Thr | Glu | Pro | Asn | Leu 340 | Gln | Asn | Ile | Pro | Ile 345 |
| Arg | Leu | Glu | Glu | Gly 350 | Arg | Lys | Ile | Arg | Gln 355 | Ala | Phe | Val | Pro | Ser 360 |
| Glu | Ser | Asp | Trp | Leu 365 | Ile | Phe | Ala | Ala | Asp 370 | Tyr | Ser | Gln | Ile | Glu 375 |
| Leu | Arg | Val | Leu | Ala 380 | His | Ile | Ala | Glu | Asp 385 | Asp | Asn | Leu | Met | Glu 390 |
| Ala | Phe | Arg | Arg | Asp 395 | Leu | Asp | Ile | His | Thr 400 | Lys | Thr | Ala | Met | Asp 405 |
| Ile | Phe | Gln | Val | Ser 410 | Glu | Asp | Glu | Val | Thr 415 | Pro | Asn | Met | Arg | Arg 420 |
| Gln | Ala | Lys | Ala | Val 425 | Asn | Phe | Gly | Ile | Val 430 | Tyr | Gly | Ile | Ser | Asp 435 |
| Tyr | Gly | Leu | Ala | Gln 440 | Asn | Leu | Asn | Ile | Ser 445 | Arg | Lys | Glu | Ala | Ala 450 |
| Glu | Phe | Ile | Glu | Arg 455 | Tyr | Phe | Glu | Ser | Phe 460 | Pro | Gly | Val | Lys | Arg 465 |

| | | | | | | | | | | | | | |
|---|---|---|---|---|---|---|---|---|---|---|---|---|---|
| Tyr | Met | Glu | Asn | Ile 470 | Val | Gln | Glu | Ala | Lys 475 | Gln | Lys | Gly | Tyr | Val 480 |
| Thr | Thr | Leu | Leu | His 485 | Arg | Arg | Arg | Tyr | Leu 490 | Pro | Asp | Ile | Thr | Ser 495 |
| Arg | Asn | Phe | Asn | Val 500 | Arg | Ser | Phe | Ala | Glu 505 | Arg | Met | Ala | Met | Asn 510 |
| Thr | Pro | Ile | Gln | Gly 515 | Ser | Ala | Ala | Asp | Ile 520 | Ile | Lys | Lys | Ala | Met 525 |
| Ile | Asp | Leu | Asn | Ala 530 | Arg | Leu | Lys | Glu | Glu 535 | Arg | Leu | Gln | Ala | Arg 540 |
| Leu | Leu | Leu | Gln | Val 545 | His | Asp | Glu | Leu | Ile 550 | Leu | Glu | Ala | Pro | Lys 555 |
| Glu | Glu | Met | Glu | Arg 560 | Leu | Cys | Arg | Leu | Val 565 | Pro | Glu | Val | Met | Glu 570 |
| Gln | Ala | Val | Thr | Leu 575 | Arg | Val | Pro | Leu | Lys 580 | Val | Asp | Tyr | His | Tyr 585 |
| Gly | Ser | Thr | Trp | Tyr 590 | Asp | Ala | Lys | | | | | | | |